United States Patent
Cai et al.

(10) Patent No.: US 9,810,619 B2
(45) Date of Patent: Nov. 7, 2017

(54) METHOD AND SYSTEM FOR SIMULTANEOUS TILT AND HEIGHT CONTROL OF A SUBSTRATE SURFACE IN AN INSPECTION SYSTEM

(71) Applicant: KLA-Tencor Corporation, Milpitas, CA (US)

(72) Inventors: Zhongping Cai, Fremont, CA (US); Jingyi Xiong, Sunnyvale, CA (US); Tyler Trytko, Sunnyvale, CA (US); Alexander Slobodov, San Jose, CA (US); Paul Doyle, San Jose, CA (US); Anatoly Romanovsky, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 296 days.

(21) Appl. No.: 14/022,305

(22) Filed: Sep. 10, 2013

(65) Prior Publication Data
US 2014/0071457 A1     Mar. 13, 2014

Related U.S. Application Data

(60) Provisional application No. 61/700,251, filed on Sep. 12, 2012.

(51) Int. Cl.
| | | |
|---|---|---|
| *G01N 21/01* | (2006.01) | |
| *G01N 21/956* | (2006.01) | |
| *G01B 5/00* | (2006.01) | |

(52) U.S. Cl.
CPC ........... *G01N 21/01* (2013.01); *G01B 5/0004* (2013.01); *G01N 21/956* (2013.01)

(58) Field of Classification Search
CPC ..... G01N 21/01; G01N 21/956; G01B 5/0004
See application file for complete search history.

(56) References Cited

U.S. PATENT DOCUMENTS

| | | | |
|---|---|---|---|
| 5,191,200 A | * | 3/1993 | van der Werf ....... G02B 21/241 250/201.4 |
| 5,805,278 A | | 9/1998 | Danko |
| 6,621,570 B1 | | 9/2003 | Danko |
| 6,702,302 B2 | | 3/2004 | Smedt et al. |

(Continued)

FOREIGN PATENT DOCUMENTS

WO     0145136 A1     6/2001

*Primary Examiner* — Hwa Lee
(74) *Attorney, Agent, or Firm* — Suiter Swantz pc llo

(57) ABSTRACT

A system for substrate tilt and focus control in an inspection system includes a dynamically actuatable substrate stage assembly including a substrate stage for securing a substrate; a tilt-height detection system including: a height detection sub-system and a tilt detection sub-system. The system further includes a first actuator configured to selectably actuate the substrate along a direction perpendicular to the surface of the substrate at a location of the substrate stage assembly; and an additional actuator configured to selectably actuate the substrate along a direction substantially perpendicular to the surface of the substrate at an additional location of the substrate stage assembly; and a MIMO tilt-focus controller communicatively coupled to the height detection sub-system, the tilt detection sub-system, the first actuator and the additional actuator.

45 Claims, 10 Drawing Sheets

(56) References Cited

U.S. PATENT DOCUMENTS

| | | |
|---|---|---|
| 7,092,082 B1 | 8/2006 | Dardzinski |
| 7,910,885 B2 | 3/2011 | Rosenberg et al. |
| 8,279,401 B2 | 10/2012 | Vervoordeldonk et al. |
| 8,351,024 B2 | 1/2013 | Den Boef |
| 8,384,882 B2 | 2/2013 | Compen et al. |
| 2007/0262268 A1* | 11/2007 | De Nivelle ........... G03F 9/7003 250/492.1 |
| 2009/0262320 A1 | 10/2009 | Staals et al. |
| 2011/0058148 A1 | 3/2011 | Baselmans et al. |

* cited by examiner

METHOD AND SYSTEM FOR SIMULTANEOUS TILT AND HEIGHT CONTROL OF A SUBSTRATE SURFACE IN AN INSPECTION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled METHOD AND SYSTEM FOR HIGH SPEED TILT AND HEIGHT CONTROL OF A SUBSTRATE SURFACE WITH A WAFER INSPECTION SYSTEM, naming Zhongping Cai, Jingyi Xiong, Tyler Trytko, Alexander Slobodov, Paul Doyle and Anatoly Romanovsky as inventors, filed Sep. 12, 2012, Application Ser. No. 61/700,251.

TECHNICAL FIELD

The present invention generally relates to a method and system for tilt and height control of a substrate surface, and, in particular, a method and system for tilt and height control of a semiconductor wafer surface during a wafer inspection process of an inspection system.

BACKGROUND

As demand for ever-shrinking semiconductor devices continues to increase, so too will the demand for improved semiconductor wafer inspection processes. The fabrication of semiconductor devices, such as logic and memory devices, typically includes processing a semiconductor wafer using a large number of semiconductor fabrication steps to form various features and multiple levels of the semiconductor devices. Optical inspection is utilized to monitor and correct the various steps of a semiconductor device manufacture process. As the dimensions of semiconductor devices continue to decrease, inspection processes become even more important to the successful manufacture of acceptable semiconductor devices. In order to improve the quality of inspection in an inspection system, the tilt and height of a semiconductor wafer surface may be controlled in order to improve focus control of a detector of the inspection, thereby improving the quality of inspection data. Typically, height and tilt of a semiconductor wafer surface are controlled independently. The independent height and tilt control make accurate compensation of tilt and height errors difficult, often leading to less than desirable levels of sensitivity and repeatability.

It would therefore be advantageous to provide a system and/or method that provides for improved height and tilt control. Accordingly, the present invention seeks to cure the deficiencies of the prior art

SUMMARY

A system for tilt and focus control in an inspection system is disclosed. In one aspect, the system may include, but is not limited to, a dynamically actuatable substrate stage assembly including a substrate stage for securing a substrate; and a tilt-height detection system including: a height detection sub-system configured to measure height of a surface of the substrate at a position of inspection of the substrate surface, the illumination emanating from an illumination source of an inspection system; and a tilt detection sub-system configured to measure tilt of the substrate disposed on the substrate stage; a first actuator operably coupled to the substrate stage assembly at a first location of the substrate stage assembly and configured to selectably actuate the substrate along a direction substantially perpendicular to the surface of the substrate at the first location of the substrate stage assembly; and an additional actuator operably coupled to the substrate stage assembly at an additional location of the substrate stage assembly and configured to selectably actuate the substrate along a direction substantially perpendicular to the surface of the substrate at the additional location of the substrate stage assembly. Further, the system may include a tilt-focus controller communicatively coupled to at least the height detection sub-system, the tilt detection sub-system, the first actuator and the additional actuator, wherein the controller is configured to: receive one or more height measurements from the height detection sub-system; receive one or more tilt measurements from the tilt detection sub-system; and responsive to the measured one or more height measurements and the one or more tilt measurements, selectably adjust an actuation state of at least one of the first actuator and the additional actuator in order to control at least one of a tilt of the substrate surface and a height of the substrate surface at the position of inspection in order to maintain the substrate surface substantially at an imaging plane of a detector of the inspection system or a focus of illumination of the inspection system within a selected tolerance level.

An inspection system with tilt and focus control is disclosed. In one aspect, the system may include, but is not limited to, an inspection sub-system including: an illumination source configured to generate illumination; a set of illumination optics configured to direct the illumination to an inspection region of a surface of a substrate disposed on a substrate stage of a dynamically adjustable substrate stage assembly; a detector configured to detect illumination reflected or scattered from the surface of the substrate; and a set of collection optics configured to collect illumination from the surface of the substrate and direct the illumination to the imaging plane of the detector. Further, the system may include a tilt-height detection system including: a height detection sub-system configured to measure height of a surface of the substrate at a position of the inspection region of the substrate surface; and a tilt detection configured to measure tilt of the substrate disposed on the substrate stage; a first actuator operably coupled to the substrate stage assembly at a first location of the substrate stage assembly and configured to selectably actuate the substrate along a direction substantially perpendicular to the surface of the substrate at the first location of the substrate stage assembly; and an additional actuator operably coupled to the substrate stage assembly at an additional location of the substrate stage assembly and configured to selectably actuate the substrate along a direction substantially perpendicular to the surface of the substrate at the additional location of the substrate stage assembly. Further, the system may include a tilt-focus controller communicatively coupled to at least the height detection sub-system, the tilt detection sub-system, the first actuator and the additional actuator, wherein the controller is configured to: receive one or more height measurements from the height detection sub-system; receive one or more tilt measurements from the tilt detection sub-system; and responsive to the measured one or more height measurements and the one or more tilt measurements, selectably adjust an actuation state of at least one of the first actuator and the additional actuator in order to control at least one of a tilt of the substrate surface and a height of the substrate surface at the position of the region of inspection in order to maintain the substrate surface substantially at an imaging plane of a detector of the inspection system or the focus of illumination of the inspection system.

A method for tilt and focus control in a substrate inspection system is disclosed. In one aspect, the method may include, but is not limited to, positioning a substrate on substrate stage of a dynamically adjustable substrate stage assembly; inspecting a region of the substrate using the inspection system; measuring height of a surface of the substrate substantially at the inspected region of the substrate; measuring tilt of the substrate; and selectably adjusting at least one of a height of a first actuation position of the substrate and a height of an additional actuation position of the substrate in order to control at least one of a tilt of the substrate surface and a height of the substrate surface at the region of inspection of the surface of the substrate in order to maintain the substrate surface substantially at the imaging plane of a detector of the inspection system or a focus of illumination of the inspection system within a selected tolerance level.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1 through 7, a system and method for dynamically adjusting tilt and height of a surface of a substrate is described in accordance with the present disclosure. The present disclosure is directed toward a system and method suitable for maintaining focus in a substrate inspection system through the dynamic adjustment of tilt and height of an inspected substrate surface. In one embodiment, the dynamic adjust of substrate tilt and height is accomplished through the measurement of substrate tilt and height at a selected region of the substrate (e.g., region of substrate inspection) coupled with feedback control of multiple substrate stage actuation devices. In this regard, a tilt and focus controller may acquire height and tilt measurement data from tilt and height sensors respectively. Responsive to the measured height and tilt of the substrate at a selected substrate location, the tilt and focus controller may conjunctively control two or more substrate stage actuation devices, within a single height/tilt control loop, to achieve a substrate height and tilt suitable for maintaining focus at the imaging plane of a detector of an associated inspection point within a selected tolerance level. Applicant notes that the present invention may be implemented in various optical inspection configurations, such as, but not limited to, brightfield wafer inspection or darkfield wafer inspection.

Figure 1:
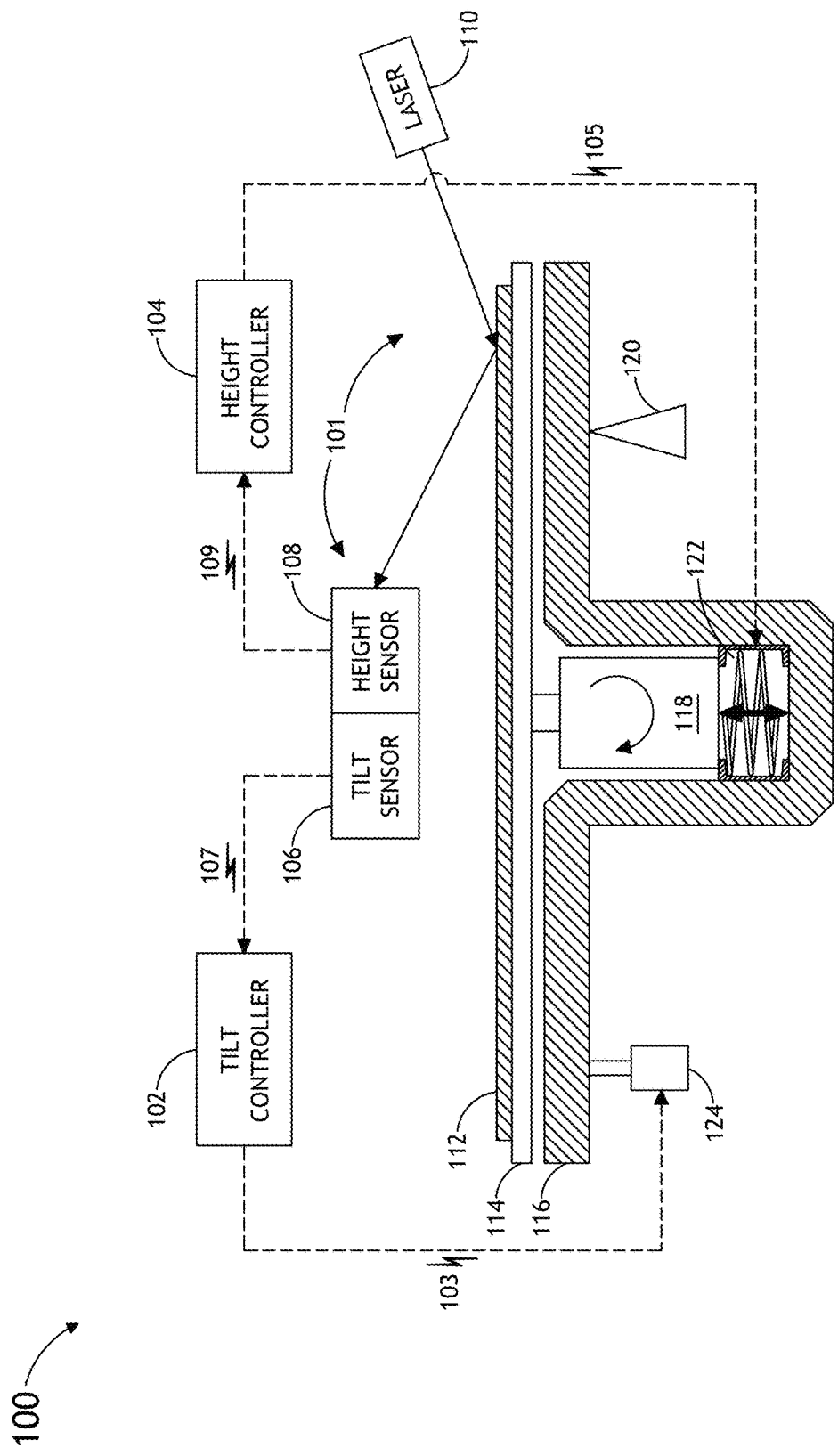
FIG. 1. Illustrates a tilt and height control system having separate tilt and height control loops in accordance with the present disclosure.

FIG. 1 illustrates a system 100 for height and tilt control including independent tilt and height control loops in accordance with the present disclosure. In one embodiment, the system 100 for tilt and height control includes an actuatable substrate assembly including a substrate stage 114 for securing a substrate 112. In another embodiment, the substrate stage assembly includes a substrate chuck 118 configured to secure the substrate 112. In another embodiment, the substrate stage assembly includes a substrate platform 116. In one embodiment, the substrate stage 114 is operably coupled to the top surface of the substrate platform 116, allowing actuation of the substrate platform 116 in order to adjust a height of one or more locations of the surface of the substrate 112 disposed on the substrate stage 114.

In one embodiment, the system 100 includes a tilt controller 102 for controlling tilt of the surface of the substrate 112 and a height controller 104 for independently controlling the height of a selected location (e.g., position of inspection) of the surface of the substrate 112. In a further embodiment, the system 100 may include a first actuator 122 (e.g., voice coil actuator) associated with the height control loop controlled via height controller 104. In another embodiment, the system 100 may include a second actuator 124 and a pivot 120 located at a selected location, whereby tilt is controlled via the tilt controller 102 by actuating the second actuator 124 along the vertical direction (i.e., perpendicular to the substrate 112 surface). In addition, the system 100 may include a tilt and height detection system 101, including a tilt sensor 106, a height sensor 108 and laser 110. It is recognized herein that the tilt-height detection system 301 described further herein may be implemented in the system 100 of the present disclosure. The details of the integrated tilt-height detection system 301 are described in greater detail further herein.

In operation, the height controller 104 may receive a detected height via signal 109 from height sensor 108. In turn, the height controller 104 may act to compensate for height error by adjusting the actuation position of actuator 122. Similarly, the tilt controller 102 may receive a detected tilt via signal 107 from tilt sensor 106. In turn, the tilt controller 102 may act to compensate for tilt by adjusting the actuation position of actuator 124 via signal 103. However, for any surface location at some distance from the pivot location 120, a tilt adjustment will lead to a change in height of the substrate 112 at that location. For example, a tilt adjustment of 1 nm/mm at 75 mm from the pivot location 120 leads to a 75 nm height change at that location. While the height control loop attempts to compensate for the tilt induced disturbance to the height control, the corresponding height residual error is relatively high.

Figure 2A:
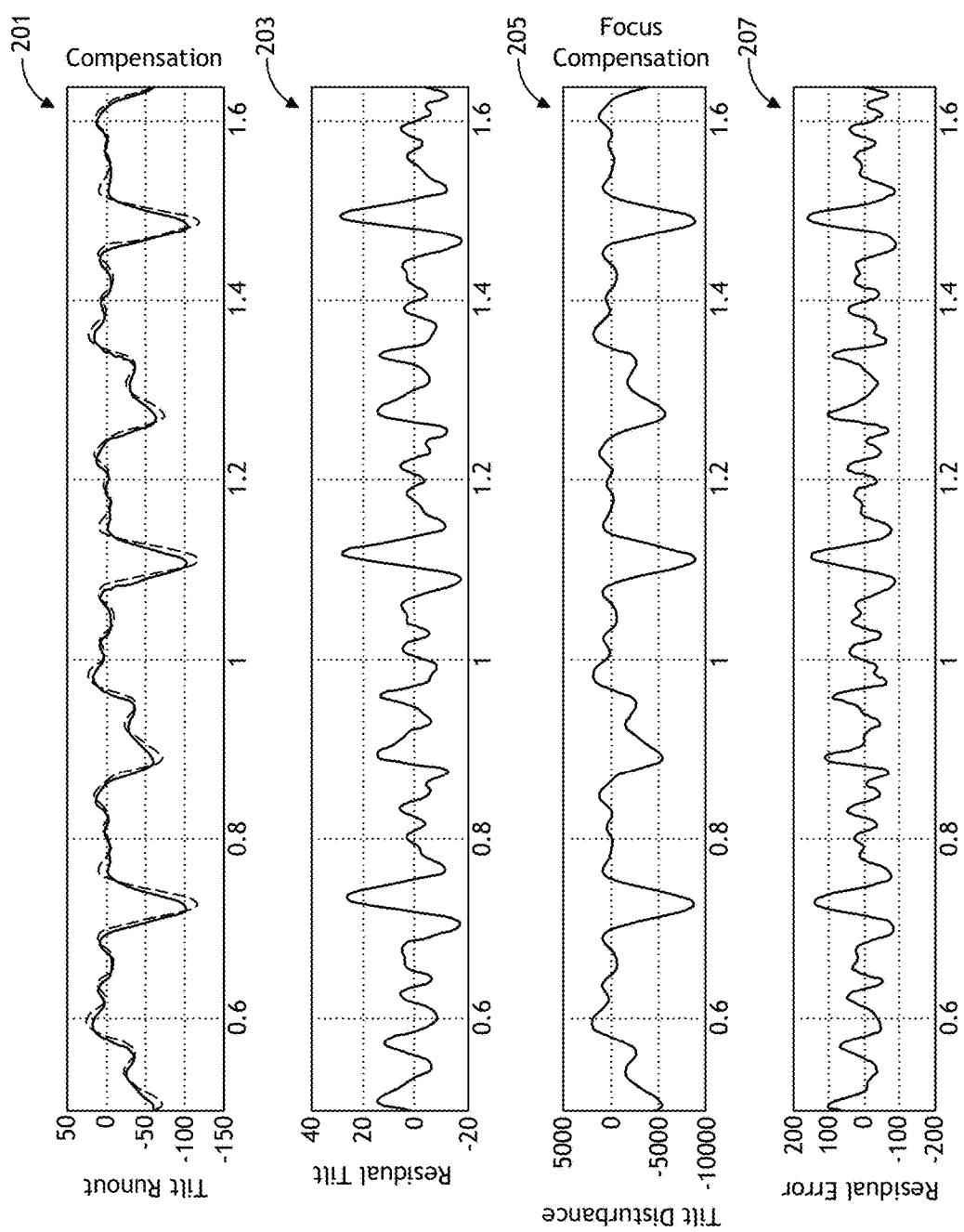
FIG. 2A illustrates tilt runout, residual tilt, tilt induced height disturbance and residual height error associated with an example operation of a tilt and height control system having separate tilt and height control in accordance with the present disclosure.

FIG. 2A illustrates an example operation of separate tilt and focus control carried out by a system consistent with system 100. The tilt control bandwidth for the tilt control loop is 30 Hz, while the height control bandwidth of the height control loop is 150 Hz, for the data of FIG. 2A. Graph 201 depicts the tilt runout (solid) and tilt compensation (dotted). The tilt runout is approximately 120 nm/mm peak-to-peak with the shown substrate motion speed. After 30 Hz bandwidth tilt control, the residual tilt is approximately 50 nm/mm peak-to-peak, as shown in Graph 203. Further, when the surface location is at 75 mm from the pivot (e.g., pivot 120 as shown in FIG. 1), the tilt control causes an approximately 11,000 nm peak-to-peak height disturbance, as shown in graph 205. Although not discernible in Graph 205, the height control loop employs a 150 Hz bandwidth height compensation to correct for the tilt induced height change. Graph 207 depicts the residual height error, which is approximately 270 nm peak-to-peak in this example. It is noted that over a 2 mm field of view, the tilt runout, in total, leads to approximately 320 nm peak-to-peak height error (total height error=270 nm peak-to-peak+(50 nm/mm peak-to-peak×2 mm)/2).

Figure 2B:
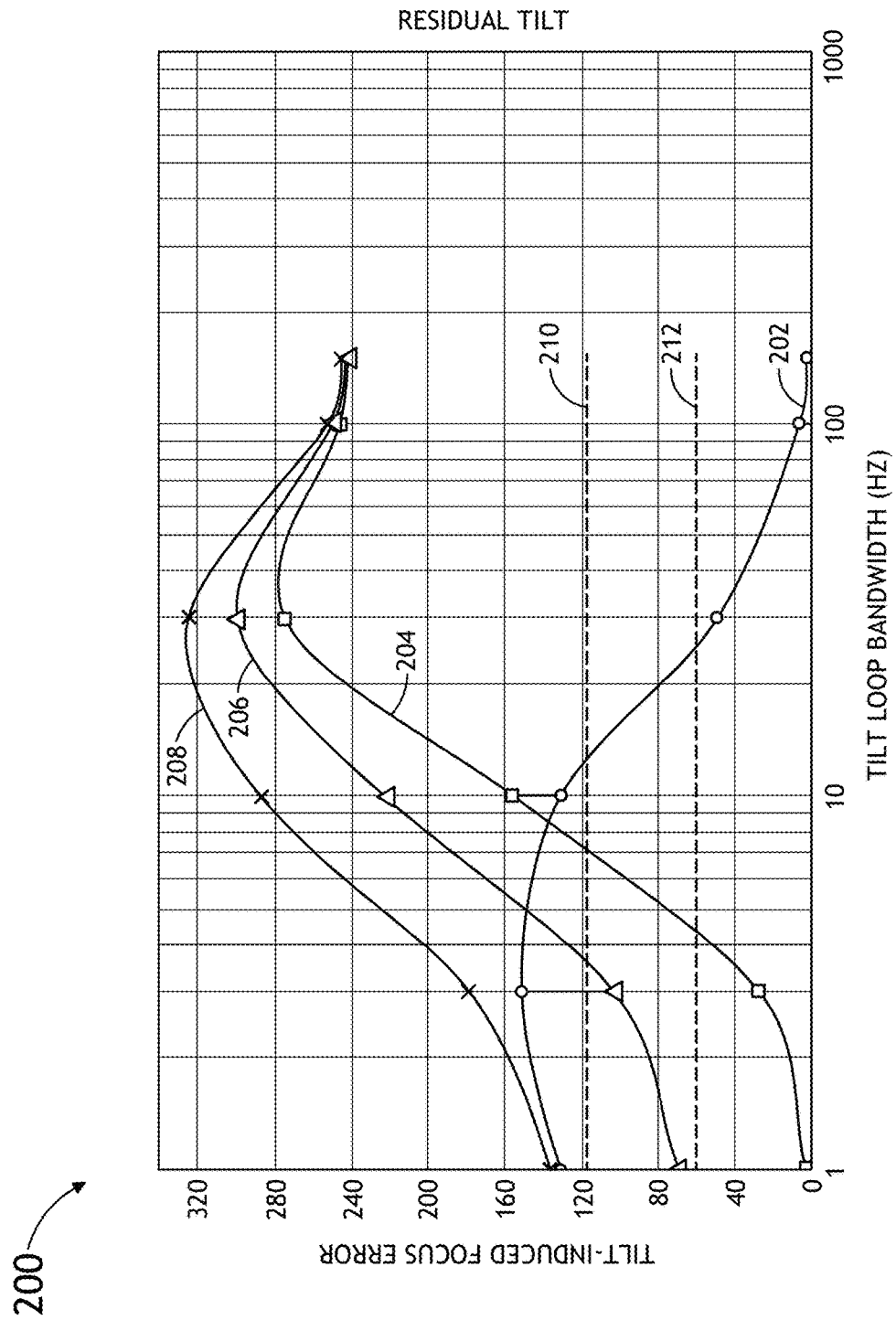
FIG. 2B illustrates residual tilt and tilt-induced focus error data acquired over a range of tilt control bandwidths via the height control system having separate tilt and height control loops in accordance with the present disclosure.

FIG. 2B illustrates the tilt-induced focus error and the residual tilt over a range of tilt control bandwidths, with the height control bandwidth fixed at 150 Hz. Curve 202 of FIG. 2B illustrates the residual tilt measured in nm/mm peak-to-peak. Curve 204 illustrates the tilt disturbance induced focus residual error. Curve 206, measured in nm peak-to-peak, illustrates the total tilt caused focus error measured over a 1 mm field of view, where line 212 shows the total tilt caused focus error for a 1 mm field of view with no tilt control. Curve 208 illustrates the total tilt caused focus error over a 2 mm field of view, where line 210 shows the total tilt caused focus error for a 2 mm field of view with no tilt control. As observed in FIG. 2A, for separate tilt and height control, low bandwidth tilt control does not compensate the tilt runout effectively, while high bandwidth tilt control causes undesirable levels of disturbance to height control.

Figure 3:
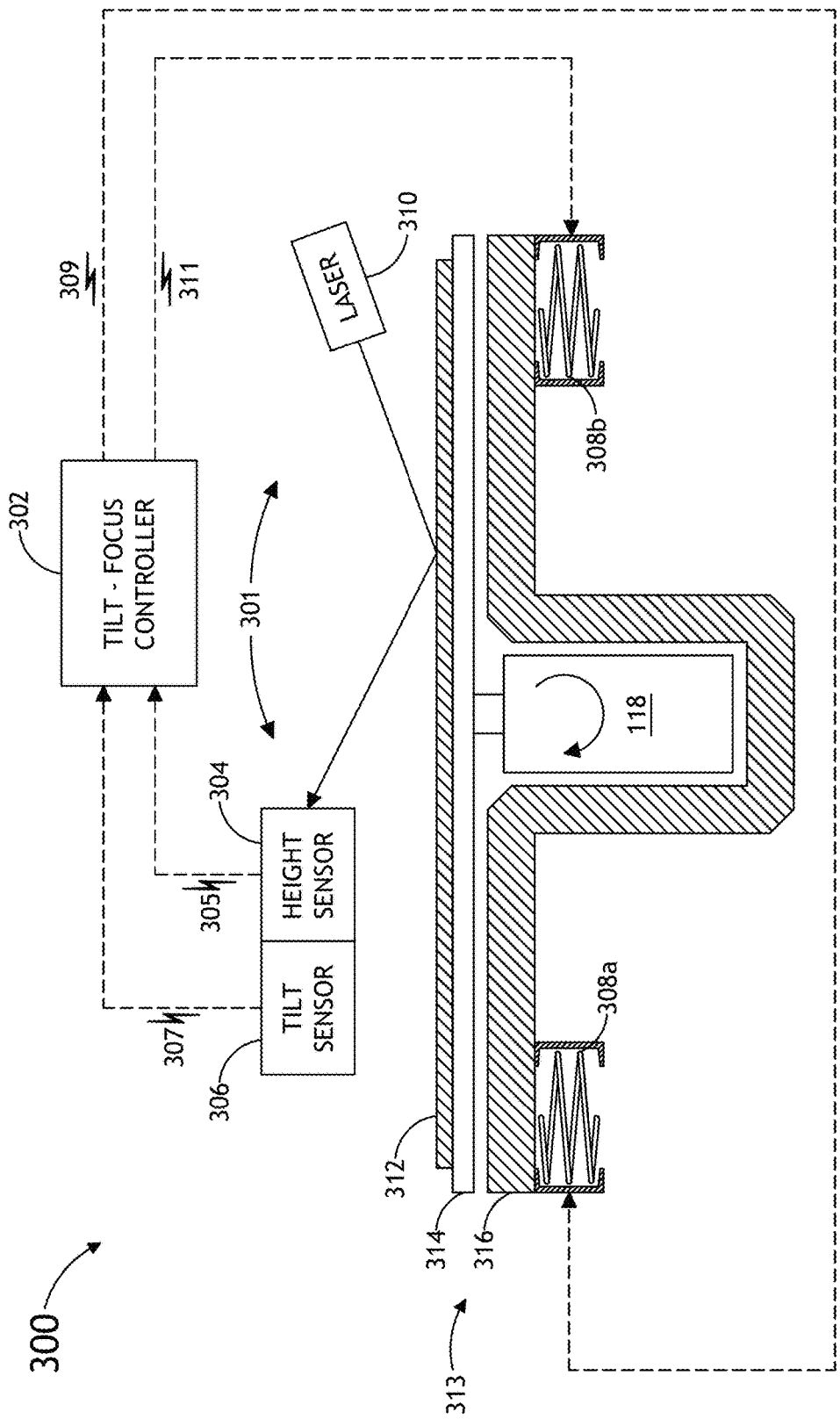
FIG. 3 illustrates a block diagram view of a system for tilt and focus control in an inspection system in accordance with one embodiment of the present disclosure.

FIG. 3 illustrates a system 300 for tilt and focus control in an inspection system in accordance with an embodiment of the present disclosure. In one embodiment, the system 300 for tilt and focus control includes a dynamically actuatable substrate stage assembly 313. In one embodiment, the substrate stage assembly 313 includes a substrate stage 314 for securing a substrate 312. In another embodiment, the substrate stage assembly 313 includes a substrate chuck 118 configured to secure the substrate 312. In another embodiment, the substrate stage assembly 313 includes a substrate platform 316. For example, the substrate platform 316 may include any substrate platform architecture known in the art suitable for actuation along a direction generally normal to the surface of the substrate 312. In this regard, the substrate stage 314 is operably coupled to the top surface of the substrate platform 316, allowing actuation of the substrate platform 316 in order to adjust a position of one or more locations of the surface of the substrate 312 disposed on the substrate stage 314.

In one embodiment, the substrate 312 includes, but is not limited to, a semiconductor wafer. For the purposes of the present disclosure the terms "substrate" and "wafer" are utilized interchangeably. As used throughout the present disclosure, the term "substrate" generally refers to a wafer formed of a semiconductor or non-semiconductor material. For example, a semiconductor or non-semiconductor material include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed. While the present disclosure focuses on the use of the present invention in the context of semiconductor wafer inspection and tilt/focus control, Applicant notes that the present invention may be extended to any substrate type known in the art.

In another embodiment, the system 300 for tilt and focus control includes two or more actuators configured to selectably actuate the substrate 312 along a direction perpendicular to the surface of the substrate 312 at a selected location of the substrate 312. In one embodiment, the system 300 includes a first actuator 308a mechanically coupled to the substrate stage assembly 313 at a first location of the substrate stage assembly 313. For example, the first actuator 308a may be mechanically coupled to the substrate stage platform 316 at a first location of the substrate stage platform 316. In this regard, the first actuator 308a may selectably adjust the substrate 312 by actuating the substrate stage platform 316 at the first location of the platform 316. In another embodiment, the system 300 may include a second actuator 308b mechanically coupled to the substrate stage assembly 313 at a second location of the substrate stage assembly 313. For example, the second actuator 308b may be mechanically coupled to the substrate stage platform 316 at a second location of the substrate stage platform 316. In this regard, the second substrate stage 308b may selectably adjust the substrate 312 by actuating the substrate stage platform 316 at the second location of the platform 316. It is noted herein that the second location associated with the second actuator 308b may be separated from the first location associated with the first actuator 308a by a selected distance. It is further noted that the first actuator 308a and the second actuator 308a may dynamically control tilt and height of the surface of the substrate 312 by simultaneously adjusting the actuation state of the first actuators 308a, 308b (i.e., actuating by the same or different degrees) at the first and second locations of the substrate stage assembly 313 respectively, as will be described in greater detail further herein.

The first actuator 308a and the second actuator 308b may include any actuator known in the art suitable for differentially actuating the substrate 312 disposed on the substrate stage assembly 313. In one embodiment, the first actuator 308a and the second actuator 308b may include, but are not limited to, one or more voice coil actuators.

In one embodiment, the system 300 includes a tilt-height detection system 301 suitable for detecting at least one of the tilt and height of the surface of the substrate 312 at a selected location.

In a further embodiment, the tilt-height detection system 301 includes a tilt detection sub-system suitable for detecting the tilt of the surface of the substrate 312 at a selected location. In a further embodiment, the tilt detection sub-system may include, but is not limited to, one or more optical sensors 306 configured to detect tilt of the surface of the substrate 312 at a selected location of the substrate 312. The one or more optical sensors 306 for use in the tilt detection sub-system of the tilt-height detection system 301 may include any optical sensor suitable for tilt detection known in the art. For example, the one or more tilt detection optical sensors 306 may include, but are not limited to, one or more photodiodes or the like. Optical configurations suitable for implementation in the tilt detection sub-system of the tilt-height detection system 301 are described in greater detail further herein.

In another embodiment, the tilt-height detection system 301 includes a height detection sub-system suitable for detecting the height of the surface of the substrate 312 at a selected location. In a further embodiment, the height detection sub-system may include, but is not limited to, one or more optical sensors 304 configured for detecting height of the surface of the substrate 312 at a selected location of the substrate 312. The one or more optical sensors 304 for use in the height detection subsystem of the tilt-height detection system 301 may include any optical sensor suitable for height detection known in the art. For example, the one or more height detection optical sensors 304 may include, but are not limited to, one or more bicell detectors, one or more line CCD detectors, one or more line CMOS detectors or the like. Optical configurations suitable for implementation in the height detection sub-system of the tilt-height detection system 301 are described in greater detail further herein.

In another embodiment, the system 300 includes a tilt-focus controller 302 configured to control the tilt and height of the surface of the substrate 312, in accordance with one embodiment of the present invention. In this regard, the tilt-focus controller 302 may adjust the tilt and/or height of the surface of the substrate 312 in order to maintain the surface of the substrate 312 at an imaging plane of a detector (not shown in FIG. 3) of an associated inspection system or at the focus of illumination of the inspection system. In this regard, the system 300 differs from that of system 100 in that the tilt and height of the substrate 312 are controlled in a Multiple Input Multiple Output tilt-focus controller 302, whereas height and tilt are controlled separately in system 100 via controllers 104 and 102 respectively. Applicant notes that in many cases the focus of illumination from the inspection system may be substantially located at the imaging plane of the detector. However, it is noted that this is not always the case as the imaging plane of the detector may be located at a position offset relative to the focus position.

In one embodiment, the tilt-focus controller 302 is communicatively coupled to the height detection sub-system and the tilt detection sub-system of the tilt-height detection system 301. For instance, the one or more height detection sensors 304 and the one or more tilt detection sensors 306 of the tilt-height detection system 301 may be communicatively coupled to the tilt-focus controller 302. In a further embodiment, the tilt-focus controller 302 is communicatively coupled to the first actuator 308a and the second actuator 308b. In this regard, the tilt-focus controller 302 of the present invention may be configured as a multiple-input-multiple-output (MIMO) controller. Further, it is recognized that the various components of the present invention may be communicatively coupled in any manner known in the art. For example, the components of the present invention may be coupled via a wireline (e.g., copper wire or optical fiber) or wireless (e.g., RF signal) connection.

In one embodiment, the tilt-focus controller 302 includes one or more processors (not shown) configured to execute a set of computer program instructions maintained on a non-transitory storage medium (i.e., memory medium). In a further embodiment, the computer program instructions are configured to cause the one or more processors of the tilt-focus controller 302 to carry out at least a portion the various steps described throughout the present disclosure.

In one embodiment, the one or more processors of the tilt-focus controller 302 are configured to receive one or more height measurements from the height detection sub-system. For example, the one or more processors of the tilt-focus controller 302 are configured to receive one or more signals 305 indicative of one or more height measurements from the height sensor 304 of the height detection sub-system. In a further embodiment, the one or more processors of the tilt-focus controller 302 are configured to receive one or more tilt measurements from the tilt detection sub-system. For example, the one or more processors of the tilt-focus controller 302 are configured to receive one or more signals 307 indicative of one or more tilt measurements from the tilt sensor 306 of the tilt detection sub-system.

Figure 6:
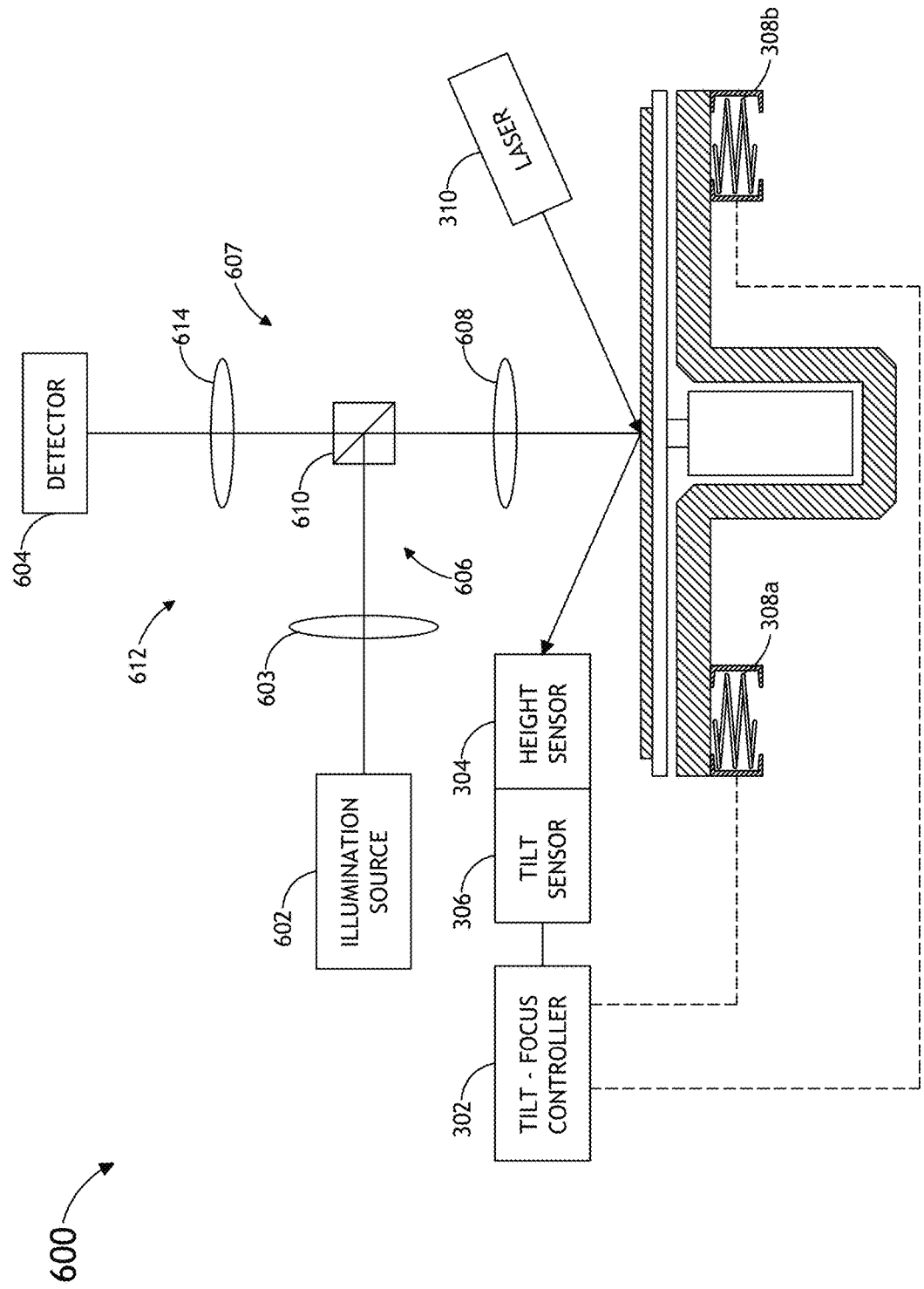
FIG. 6 illustrates a block diagram view of an inspection system with tilt-focus control in accordance with one embodiment of the present disclosure.

In another embodiment, in response to the measured one or more height measurements and the one or more tilt measurements, the tilt-focus controller 302 may selectively adjust an actuation state of at least one of the first actuator 308a and the second actuator 308b in order to control the tilt or the height of the substrate 312 surface at a position of inspection (or illumination) of the inspection system. For example, in response to the received signals 305 and 307, the one or more processors of the tilt-focus controller 302 may transmit at least one of a first signal 309 and a second signal 311 to the first actuator 308a and the second actuator 308b respectively. In this regard, the tilt-focus controller 302 may adjust an actuation state of at least one of the first actuator 308a or the second actuator 308b. For example, the tilt-focus controller 302 may direct either the first actuator 308a or the second actuator 308b to move up or down (i.e., generally perpendicular to the surface of the substrate 312), thereby adjusting the height or tilt of the surface of the substrate 312 in order to maintain the surface of the substrate 312 substantially at an imaging plane of a detector of the inspection system (e.g., inspection system as shown in FIG. 6) within a selected tolerance level (e.g., adequate focus for image quality needs) or the focus of the illumination of the inspection system.

It is noted herein that while the present invention is generally described in the context of two actuators (e.g., 308a and 308b) this should not be interpreted as a limitation. It is recognized herein that the present invention may be extended to encompass tilt-focus control systems having more than two actuators. For instance, a control system having 3 actuators, 4 actuators or up to and including N actuators is within the scope of the present invention. It is further noted that while the implementation of 2 actuators as described throughout the present invention allows for control of tilt and/or height along one direction, which may be aligned along the inspection scan direction, the use of more than 2 actuators may allow for tilt/height control along both directions (e.g., X-direction and Y-direction) within the plane of the substrate 312.

In one embodiment, the height detection sub-system and the tilt detection sub-system are optically integrated. In this regard, the height detection sub-system and the tilt detection sub-system may share an illumination source to form an optically integrated tilt-height detection system 301. In a further embodiment, the tilt detection sub-system may include a differential interference contrast (DIC) based tilt detection sub-system.

Figure 4A:
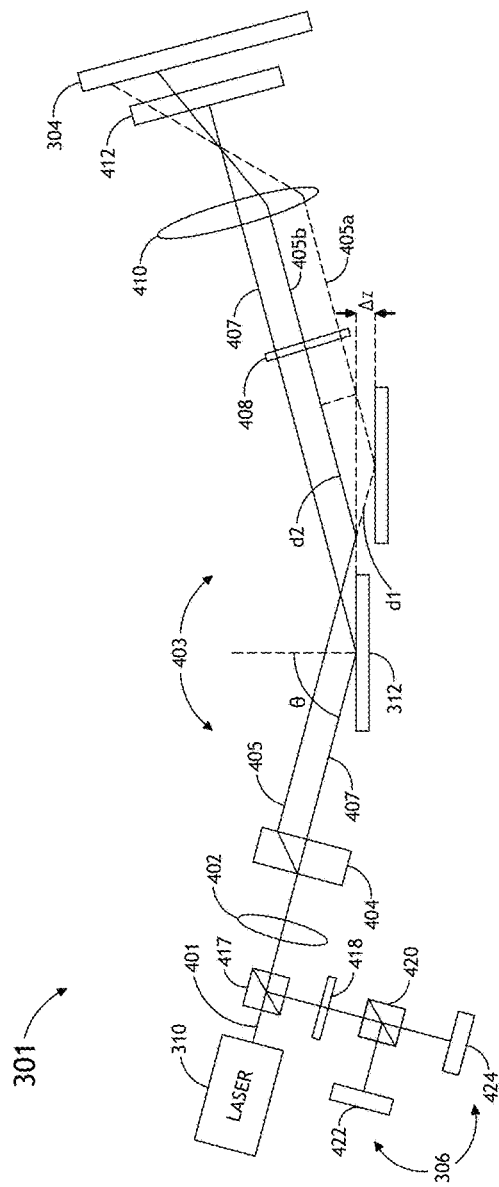
FIG. 4A illustrates an integrated tilt-height detection system in accordance with one embodiment of the present disclosure.
Figure 4B:
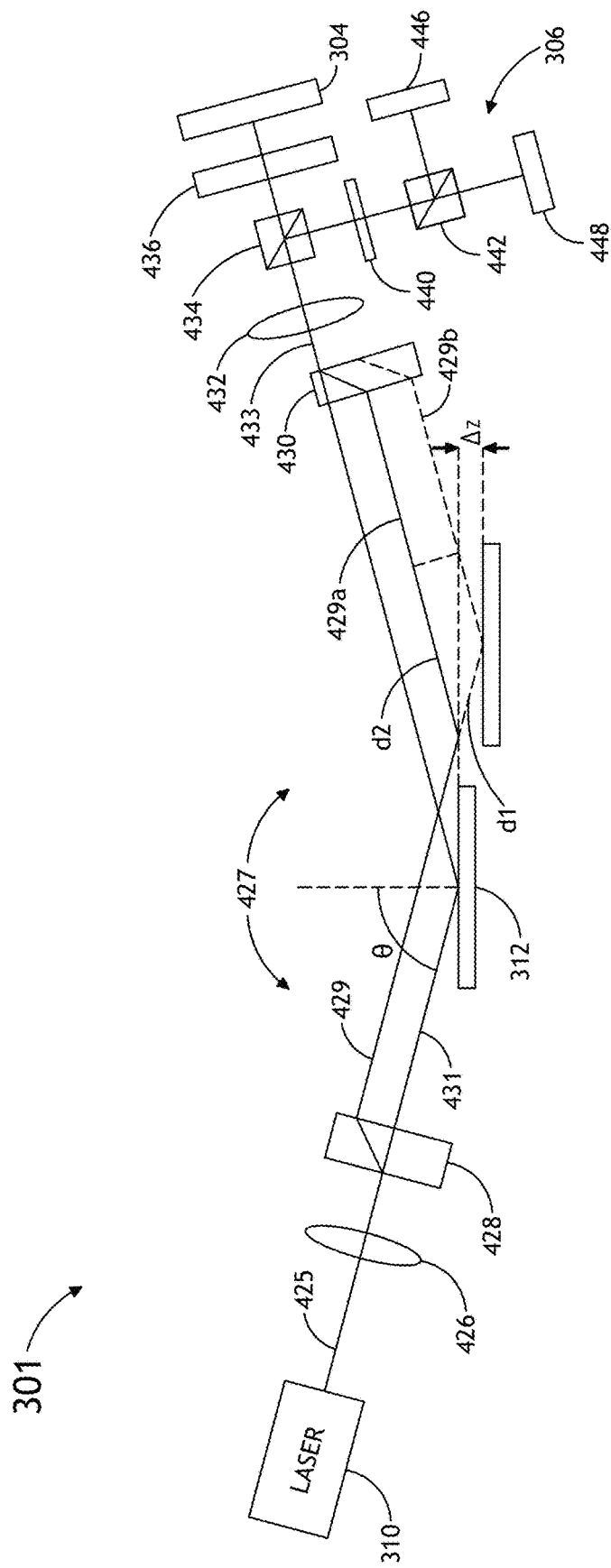
FIG. 4B illustrates an integrated tilt-height detection system in accordance with one embodiment of the present disclosure.

FIGS. 4A and 4B illustrate a tilt-height detection system 301 configured to implement a differential interference contrast (DIC) technique for tilt detection in accordance with one or more embodiments of the present disclosure. FIG. 4A illustrates an optically integrated tilt-height detection system 301 utilizing a double passed beam technique in accordance with one embodiment of the present disclosure. In one embodiment, the optically integrated tilt-height detection system 301 of FIG. 4A includes a laser source 310 suitable for generating a light beam 401. For example, the laser source 310 may generate a laser beam having a selected wavelength (e.g., 640 nm). By way of another example, the laser beam may be linearly polarized (e.g., 45 degrees).

In a further embodiment, the detection system 301 includes an oblique differential interferometer optical sub-system 403. In one embodiment, the oblique differential interferometer optical sub-system 403 includes an optical element 404 configured to separate the light beam 401 into a first beam 405 and a second beam 407 and direct the first beam 405 and the second beam 407 onto the substrate 312 at the position of illumination from the inspection system at an angle of incidence, represented as θ.

Generally, in cases where a height difference of Δz is observed at the wafer surface, the optical path length difference between the first beam 405 and the second beam 407 is given by:

$$OPD = 2d_1 - d_2 = 2\frac{\Delta z}{\cos\theta} - 2\Delta z \tan\theta \cdot \sin\theta = 2\Delta z \cos\theta$$

Where d1 is the path distance for the first beam 405 and d2 is the path distance for the second beam 407. For the double-passed beam case of FIG. 4A the optical path difference is given by twice of that provided above:

OPD=4Δz cos θ

Further, the optical element 404 is configured to orthogonally polarize and transversely separate the first beam 405 and second beam 407. For example, the first beam 405 may be s-polarized, while the second beam 407 is p-polarized, with the beams being displaced spatially from one another. The optical element 404 may include any optical device known in the art suitable for splitting a beam into two transversely separated beams (e.g., transversely separate beams oriented substantially parallel to one another) having orthogonal polarization. In one embodiment, the optical element 404 may include a Wollaston prism.

In another embodiment, the oblique differential interferometer optical sub-system 403 includes a reflection-transmission flat 408 configured to reflect back a portion of the first beam 405a/405b and the second beam 407 received from the substrate 312 surface back to the optical element 404. For example, the reflection-transmission flat 408 may include a 50% reflection/50% transmission flat suitable for reflecting 50% of the beams.

In a further embodiment, the optical element 404 is configured to recombine the portion of the first beam 405 and the second beam 407 reflected back to the optical element 404 into a recombined beam.

In another embodiment, the polarization components of the recombined beam may be analyzed by the tilt-focus controller 302 in order to determine a tilt of the surface of the substrate 312. In one embodiment, the one or more tilt sensors 306 of the oblique differential interferometer optical sub-system 403 may include a first sensor 422 for detecting light of a first polarization of the recombined beam and a second sensor 424 for detecting light of a second polarization of the recombined beam. For example, at least one of the first sensor and second sensor 422, 424 may include one or more photodiodes. In another embodiment, the sub-system 403 may include a beam splitter 417 configured to redirect at least some of the combined light through the polarizer 418 and to the polarized beam splitter 420. The polarized beam splitter 420 may be configured to direct light of the first polarization of the recombined beam to the first detector 422 and light of the second polarization of the recombined beam to a second detector 424.

In another embodiment, tilt-focus controller 302 is further configured to compare the light of the first polarization detected by the first sensor 422 and the light of the second polarization detected by the second sensor 424 in a differential interference detection process to determine a tilt of the substrate 312 surface.

In another embodiment, the integrated tilt-height detection system 301 includes a height detection sub-system including one or more height sensors 304 for height detection of the surface of the substrate 312. In a further embodiment, one of the laser beams transmitted by the reflection-transmission flat 408 may be used for the purposes of height detection of the surface of the substrate 312. In one embodiment, the height detection sub-system of the tilt-height detection system 301 may include a polarizer 412 for selecting a polarization state of the beams to transmit to the height sensor 304. In this regard, height sensor 304 may utilize one or more of the transmitted beams to detect a relative position of the light beam reflected from the surface of the substrate 312. Further, the tilt-focus controller 302 is configured to determine a height value of the surface of the substrate 312 based on the measured relative position of the light beam at the height sensor 304. As previously discussed, the height sensor 304 may include any optical sensor known in the art for height detection. For example, the height sensor 304 may include, but is not limited to, a bicell detector. In other embodiments, although not shown, the height sensor 304 may include one or more line CCD detectors or one or more line CMOS detectors.

In another embodiment, the tilt-height detection system 301 may include any number of optical elements for directing and processing illumination from the laser source 310 to the surface of the substrate 312. For example, as shown in FIG. 4A, the tilt-height detection system 301 may include, but is not limited to, a set of illumination optics 402 suitable for directing and/or focusing light from the light beam 401 onto the substrate 312 surface. In another embodiment, the tilt-height detection system 301 may include any number of optical elements for directing and processing illumination from reflected from the surface of the substrate 312 to the height sensor 304. For example, as shown in FIG. 4A, the detection system 301 may include, but is not limited to, a set of illumination optics 410 suitable for directing and/or focusing light reflected from the surface of the substrate 312 onto a portion of the height sensor 304.

FIG. 4B illustrates an optically integrated tilt-height detection system 301 in a non-double passed beam configuration in accordance with one embodiment of the present disclosure. In one embodiment, the integrated tilt-height detection system 301 of FIG. 4B includes laser source 310 for generating a linearly polarized beam, as described previously herein.

In one embodiment, the oblique differential interferometer optical sub-system 427 of the tilt-height detection system 301 of FIG. 4B includes an optical element 428 configured to separate the light beam 425 into a first beam 429 and a second beam 431 and direct the first beam 429 and the second beam 431 onto the substrate 312 at the position of illumination from the inspection system at an angle of incidence, represented as θ, in a manner similar to that described above. Further, the optical element 428 is configured to orthogonally polarize and transversely separate the first beam 429 and second beam 431, as described previously herein. The optical element 428 may include any optical device known in the art suitable for splitting a beam into two transversely separated beams (e.g., transversely separate beams oriented substantially parallel to one another) having orthogonal polarization. In one embodiment, the optical element 428 may include a Wollaston prism.

In another embodiment, the optical sub-system 427 includes a second optical element 430 configured to form a recombined beam 433 by combining the first beam 429a/429b and the second beam 431 upon reflection from the substrate 312 surface. The optical element 430 may include any optical device known in the art suitable for combining, or "recombining," two transversely separated beams. In one embodiment, the optical element 430 may include a second Wollaston prism.

In another embodiment, the optical sub-system 427 may include a beam splitter 434 configured to split off a portion of the recombined beam 433 for the purposes of tilt detection (via sensors 446 and 448), while allowing some light through unimpeded for the purposes of height detection (via height sensor 304).

In another embodiment, the polarization components of the recombined beam 433 may be analyzed by the tilt-focus controller 302 in order to determine a tilt of the surface of the substrate 312. In one embodiment, the one or more tilt sensors 306 of the oblique differential interferometer optical sub-system 427 may include a first sensor 446 for detecting light of a first polarization of the recombined beam 433 and a second sensor 448 for detecting light of a second polarization of the recombined beam 433. For example, at least one of the first sensor and second sensor 446, 448 may include one or more photodiodes. In another embodiment, the beam splitter 434 may direct light from the recombined beam 433 through polarizer 440 and a polarized splitter 442 configured to direct light of the first polarization of the recombined beam 433 to the first detector 446 and light of the second polarization of the recombined beam 433 to a second detector 448. In another embodiment, tilt-focus controller 302 is further configured to compare the light of the first polarization detected by the first sensor 446 and the light of the second polarization detected by the second sensor 448 in a differential interference detection process to determine a tilt of the substrate 312 surface.

In another embodiment, as described previously herein, the integrated tilt-height detection system 301 includes a height detection sub-system including one or more height sensors 304 for height detection of the surface of the substrate 312. In a further embodiment, one of the beam components (e.g., first beam 429a/429b or second beam 431) of the recombined beam 433 may be used for the purposes of height detection of the surface of the substrate 312. In another embodiment, the tilt-height detection system 301 may include a polarizer 436 prior to the height sensor 304. As described previously herein, the height sensor 304 may utilize one or more of the components reflected from the surface of the substrate 312 to detect a relative position of the given beam component from the surface of the substrate 312. In turn, the tilt-focus controller 302 is configured to determine a height value of the surface of the substrate 312 based on the measured relative position of the beam component at the height sensor 304. As previously discussed, the height sensor 304 may include any optical sensor known in the art for height detection. For example, the height sensor 304 may include, but is not limited to, a bicell detector. In other embodiments, although not shown, the height sensor 304 may include one or more line CCD detectors or one or more line CMOS detectors.

In another embodiment, the tilt-height detection system 301 may include any number of optical elements for directing and processing illumination from the laser source 310 to the surface of the substrate 312. For example, as shown in FIG. 4B, the detection system 301 may include, but is not limited to, a set of illumination optics 426 suitable for directing and/or focusing light from the laser beam onto the substrate 312 surface. In another embodiment, the tilt-height detection system 301 may include any number of optical elements for directing and processing illumination reflected from the surface of the substrate 312 to the height sensor 304. For example, as shown in FIG. 4B, the detection system 301 may include, but is not limited to, a set of illumination optics 432 suitable for directing and/or focusing light reflected from the surface of the substrate 312 onto a portion of the height sensor 304.

It is noted herein that the non-double pass configuration depicted in FIG. 4B is particularly advantageous in settings where issues related to low wafer reflectivity issues exist, since the beams utilized for analyze are only reflected from the surface of the substrate 312 once.

The maximum detection range for DIC exists when:

$$\Delta z = \frac{\lambda}{4\cos\theta}$$

Where λ is the wavelength of the laser source 310. For example, when λ=640 nm and θ=70°, the maximum Δz is approximately 468 nm. Further, for a 4 mm field of view, this creates a maximum tilt angle of approximately 117 μrad peak-to-peak.

It is noted herein that while the description of FIGS. 4A and 4B of the present disclosure have focused on the implementation of the present invention utilizing an integrated tilt-height detection system 301 (i.e., tilt detection sub-system and height detection sub-system share an illumination and one or more optical elements), it is recognized that this is not a limitation on the present invention. It is recognized herein, although not shown, that the height detection sub-system and the tilt detection sub-system of system 301 need not be integrated. In this regard, each of the height detection sub-system and the tilt detection sub-system may possess their own illumination source and their optical elements may operate independently.

It is noted that while the tilt-height detection system 301 has been described primarily in the context of the system 300 of the present disclosure, it is further recognized herein that the tilt-height detection system 301 may be implemented in the context of the separate tilt control and height control system 100, described previously herein. It is further recognized herein that the integrated tilt-height detection system 301 described in FIGS. 4A and 4B may be extended to any tilt-height detection scenario and is not limited to the tilt/height control features described herein.

Figure 5A:
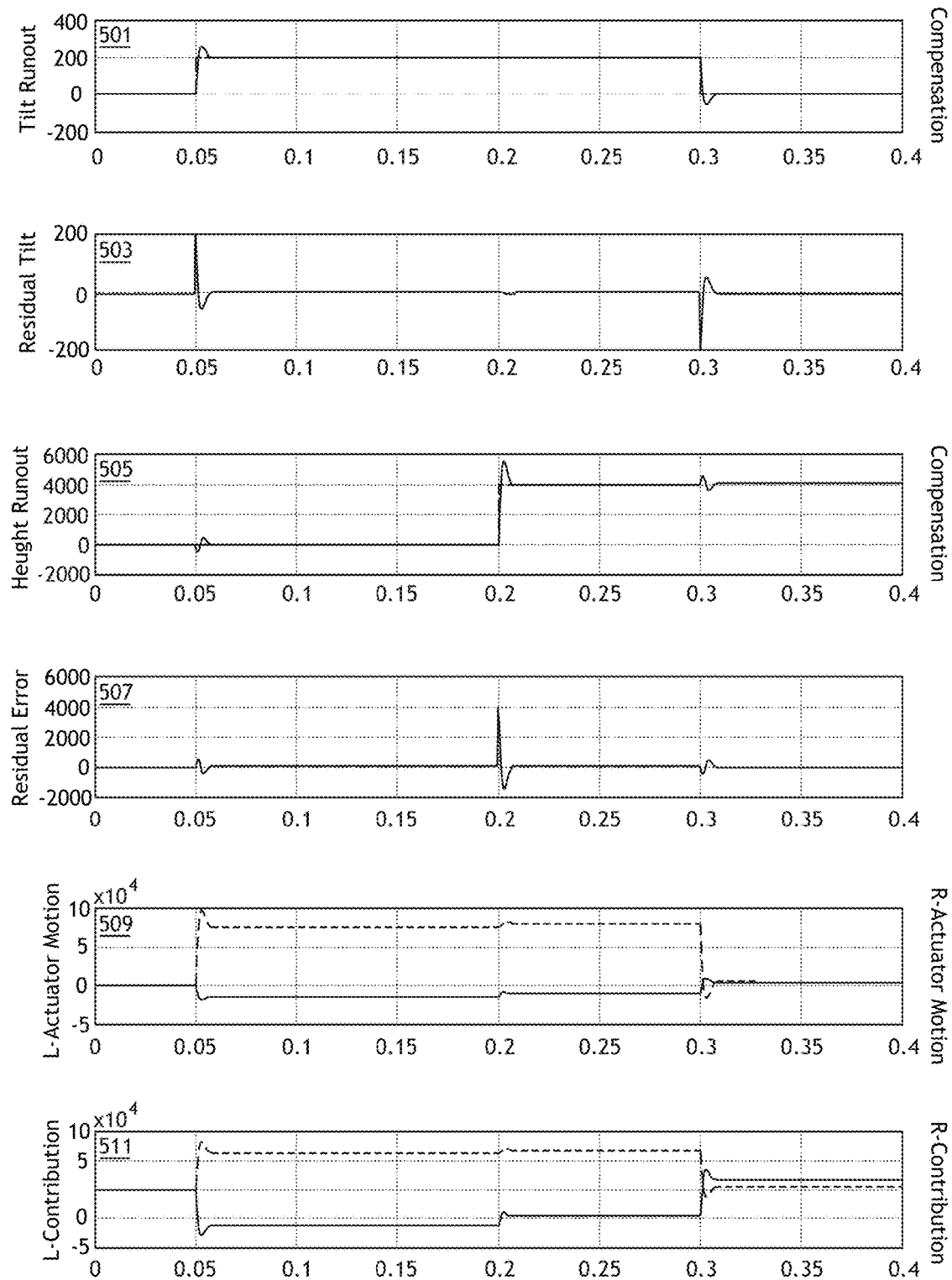
FIG. 5A illustrates tilt runout, residual tilt, tilt induced height disturbance and residual height error associated with an example operation of a tilt and height control system having separate tilt and height control in accordance with the present disclosure.

FIG. 5A illustrates an example operation of combined tilt/focus MIMO controller by system 300. In this example, the bandwidth for both tilt and height control is 150 Hz. Applicants further note that the tilt runout of 120 nm/mm peak-to-peak is the same tilt runout associated with the data sets depicted in FIG. 2A. In the response example of FIG. 5A, the first actuator 308a and the second actuator 308b of the system 300 are separated by approximately 450 mm, whereby the inspection location is positioned at approximately 75 mm to the left of the second actuator 308b. Graph 501 depicts tilt runout (dotted) and tilt compensation (solid). As shown, a 200 µRad tilt run out step occurs at time 0.05 seconds. In turn, the tilt compensation by the system 300 sufficiently stabilizes at approximately 0.059 seconds. The residual tilt is illustrated in Graph 503. The tilt step response causes an approximately 1 µm peak-to-peak height error disturbance. To complete this step, the first actuator 308a may move up by 75 µm, while second actuator 308b moves down by 15 µm, as shown in Graph 509. However, the contributions to the height at the inspection location are +12.5 µm and −12.5 µm, respectively, as shown in Graph 511. As such, the overall height remains unchanged.

Height runout (dotted) and height error compensation are illustrated in Graph 505, with residual focus error illustrated in Graph 507. At time 0.2 second, a 4 µm height run out step occurs, as shown in Graph 505. In turn, the height compensation by the system 300 stabilizes at approximately 0.209 seconds. This height step response causes an approximately 8 µRad peak-to-peak tilt error disturbance. To complete this step, both actuators move up by 4 µm, as shown in Graph 511, leaving the tilt of the surface unchanged. Applicant notes that the above description is provided for illustrative purposes only and it is noted herein that the present invention is not limited to the specific operation described above. It is recognized that the principles described above may be extended to a large number of tilt correction/height correction scenarios, which are within the scope of the present invention.

Figure 5B:
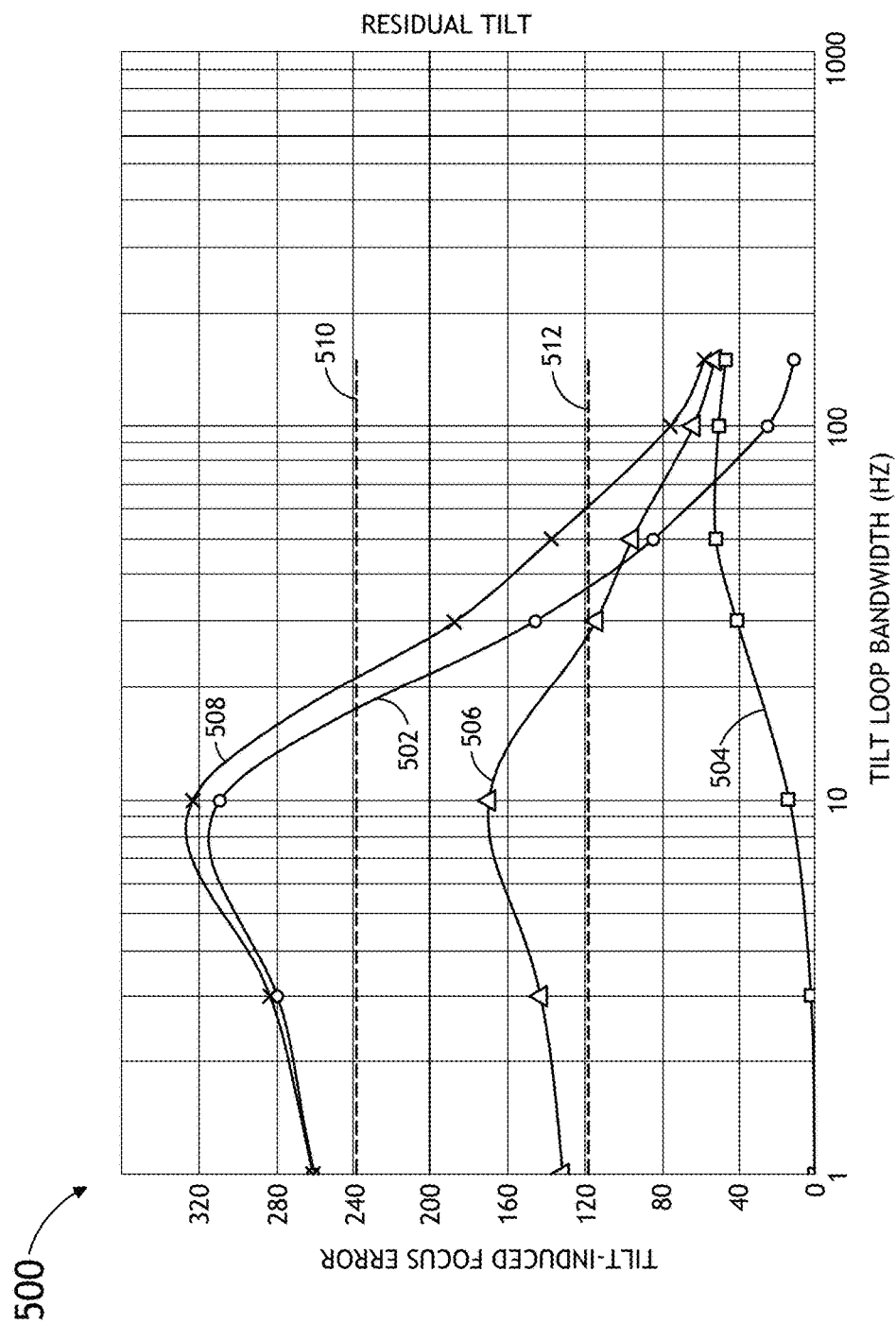
FIG. 5B illustrates various tilt and height runout and correction data associated with an example operation of the system for coupled tilt and focus control via a tilt-focus controller in accordance with one embodiment of the present disclosure.

FIG. 5B illustrates the tilt-induced height error and the residual tilt over a range of tilt control bandwidths (measured in Hz). Applicants note that the height control bandwidth for the data of FIG. 5 is 150 Hz, as in FIG. 2. Curve 502 of FIG. 5B illustrates the residual tilt measured in nm/mm peak-to-peak. Curve 504 illustrates the tilt disturbance induced focus residual error. Curve 506, measured in nm peak-to-peak, illustrates the total tilt caused focus error measured over a 1 mm field of view, where line 512 shows the total tilt caused focus error for a 1 mm field of view with no tilt control. Curve 508 illustrates the total tilt caused focus error over a 2 mm field of view, where line 510 shows illustrates the total tilt caused focus error for a 2 mm field of view with no tilt control. As shown, at 150 Hz tilt control bandwidth, the residual tilt is approximately 5.2 nm/mm peak-to-peak, which causes 5.2 nm peak-to-peak height error over a 2 mm field of view. Further, the tilt response causes approximately 23.5 nm peak-to-peak height error disturbance. As such, the total tilt-induced height error is approximately 28.7 nm peak-to-peak. Thus, it is apparent that the tilt control method and architecture of the present invention significantly reduces the total tilt-induced height error, which is approximately 120 nm peak-to-peak without tilt control.

FIG. 6 illustrates a block diagram view of an inspection system equipped with tilt-focus control system 301, in accordance with one embodiment of the present invention. In one embodiment, the inspection system 600 may include an inspection sub-system 612 and the tilt-focus control system 301 described previously herein. The description of the tilt-focus control system 301 should be interpreted to extend to the inspection system 600.

In one embodiment, the inspection sub-system 612 includes an illumination source 602. The illumination source 602 may include any illumination source known in the art. For example, the illumination source 602 may include a narrowband source (e.g., laser) or a broadband source (e.g., laser produced plasma source or discharge produced plasma source).

In another embodiment, the inspection sub-system 612 includes a set of illumination optics 606 configured to direct the illumination to an inspection region of a surface of a substrate 312 disposed on a substrate stage 314 of a dynamically adjustable substrate stage assembly 313. For example, the set of illumination optics 606 may include, but are not limited to, one or more lenses 603 for focusing the illumination from the illumination source 602 onto an inspection region of the substrate 312 surface. By way of another example, the set of illumination optics 606 may include, but are not limited to, a beam splitter 610 for directing at least a portion of the illumination from the illumination source 602 onto an inspection region of the substrate 312 surface.

In another embodiment, the inspection sub-system 612 includes a detector 604 configured to detect illumination reflected or scattered from the surface of the substrate 312. The detector 604 may include any imaging detector known in the art. For example, the detector 604 may include, but is not limited to, a CCD detector, a TDI-CCD detector, a CMOS detector and the like.

In another embodiment, the inspection sub-system 612 includes a set of collection, or imaging, optics 607 configured to collect illumination reflected or scattered from the surface of the substrate 312 and direct the illumination to the imaging plane of the detector 604. For example, the collection optics 607 may include, but are not limited to, a primary objective lens 608 for collecting light from the surface of the substrate 312 and directing it to the detector 604. By way of another example, the collection optics 607 may include, but are not limited to, an imaging lens 614 for imaging the inspection region of the substrate 312 onto the imaging plane of the detector 604.

Applicant notes that the optical configuration depicted in FIG. 6 is provided merely for illustrative purposes and should not be interpreted as limiting. In a general sense, the inspection system 600 of the present invention may include any set of imaging and optical elements suitable for imaging the surface of the substrate 312. For example, the inspection sub-system 612 may be configured to perform brightfield or darkfield inspection. In addition, while the inspection sub-system 612 of FIG. 6 has been depicted with normal incidence, this should not be interpreted as a limitation, as it is recognized herein that the inspection sub-system 612 may be configured for normal or oblique incidence. Examples of currently available wafer inspection tools are described in detail in U.S. Pat. No. 7,092,082, U.S. Pat. No. 6,702,302, U.S. Pat. No. 6,621,570 and U.S. Pat. No. 5,805,278, which are each herein incorporated by reference.

Figure 7:
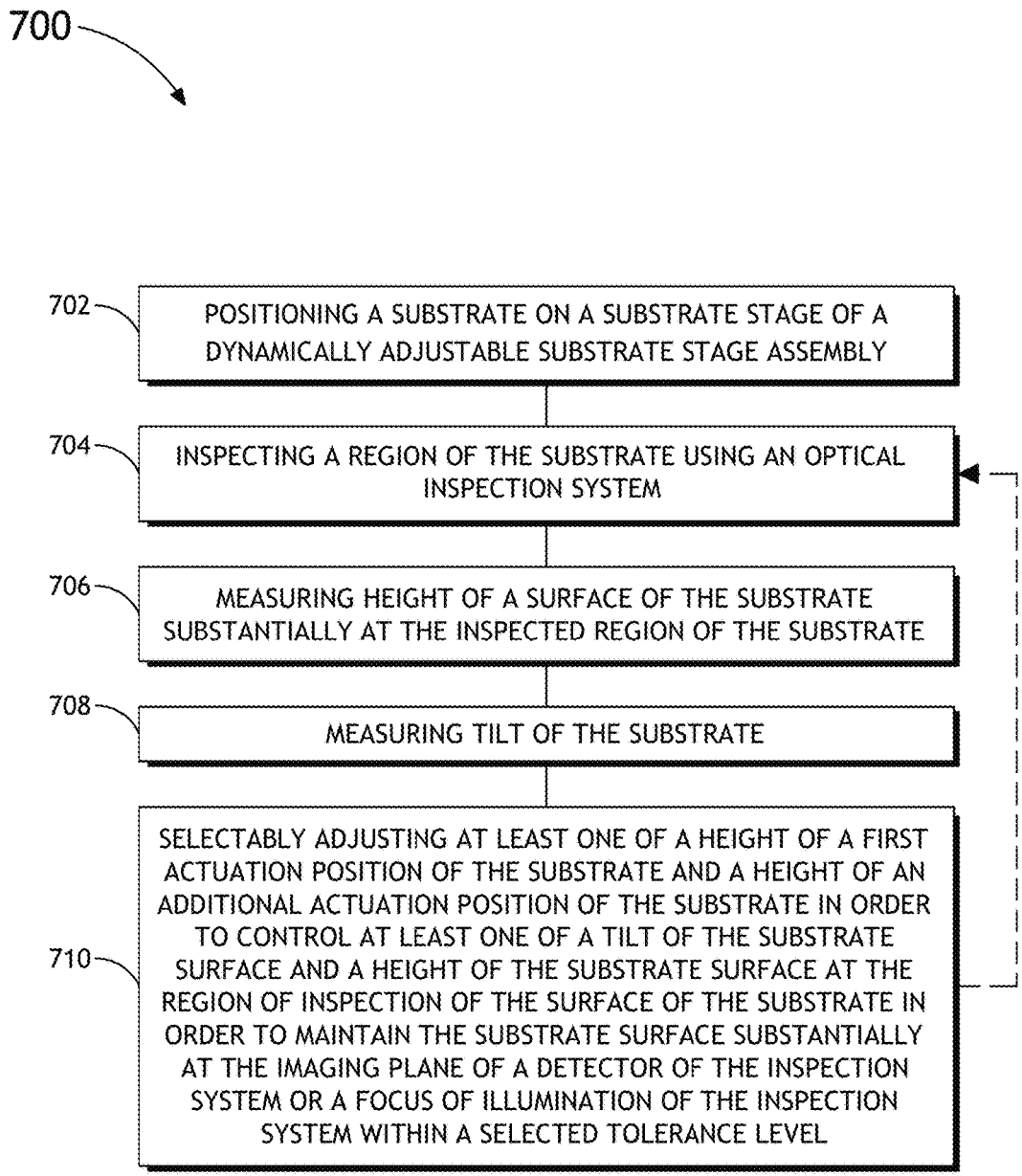
FIG. 7 illustrates a method for tilt-focus control in an inspection system, in accordance with one embodiment of the present disclosure.

FIG. 7 illustrates a method 700 for tilt and height control in a substrate inspection system in accordance with one embodiment of the present disclosure. It is noted herein that method 700 of the present disclosure may be carried utilizing one or more of the systems or sub-systems described previously herein, however the various structural elements and configurations described previously herein should not be interpreted as limitations on method 700 as it is anticipated that other structures and configurations may be used to carry out method 700.

In step 702, a substrate 312 is positioned on substrate stage 314 of a dynamically adjustable substrate stage assembly 313. In step 704, a region of the substrate 312 is inspected using the inspection system 600. In step 706, the height the surface of the substrate 312 is measured at the location of the inspected region of the substrate 312. In step 708, the tilt of the substrate 312 is measured. In step 708, the height of a first actuation position of the substrate 312 and a height of a second actuation position of the substrate 312 is selectively adjusted (e.g., adjusted using actuators 308a/308b) in order to control the tilt of the substrate 312 surface or the height of the substrate 312 surface at the region of inspection of the surface of the substrate 312 in order to maintain the substrate 312 surface at the imaging plane of the detector 604 of the inspection system 600 or at the focus of the illumination beam of the inspection system 600 within a selected tolerance level. In addition, it is noted that following adjustment of the actuators 308a and 308b the inspection process may be carried out again. Further, it is noted herein that the order of the steps of method 700 is not limiting as it is recognized that the inspection and height adjustments processes can be carried out in any order or simultaneously.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system for tilt and focus control in an inspection system, comprising:
    a dynamically actuatable substrate stage assembly including a substrate stage for securing a substrate;
    a laser source configured to generate a light beam;
    a tilt-height detection system including:
        a height detection sub-system comprising: an optical assembly; and a height sensor, wherein the height sensor comprises one or more optical sensors configured to measure height of a surface of the substrate at a position of inspection of the substrate surface; and
        a differential interference contrast tilt detection sub-system configured to measure tilt of the substrate disposed on the substrate stage, wherein the differential interference contrast tilt detection sub-system comprises an oblique differential interferometer optical assembly, wherein the oblique differential interferometer optical assembly comprises a first optical sensor and a second optical sensor;
    a first actuator operably coupled to the substrate stage assembly at a first location of the substrate stage assembly and configured to selectively actuate the substrate along a direction substantially perpendicular to the surface of the substrate at the first location of the substrate stage assembly;
    an additional actuator operably coupled to the substrate stage assembly at an additional location of the substrate stage assembly and configured to selectively actuate the substrate along a direction substantially perpendicular to the surface of the substrate at the additional location of the substrate stage assembly; and
    a tilt-focus controller including one or more processors configured to execute a set of program instructions stored in memory, the tilt-focus controller communicatively coupled to at least the height detection sub-system, the tilt detection sub-system, the first actuator and the additional actuator, wherein the set of program instructions are configured to cause the one or more processors to:
        receive one or more height measurements from the height detection sub-system;
        receive one or more tilt measurements from the tilt detection sub-system; and
        responsive to the measured one or more height measurements and the one or more tilt measurements, selectively adjust an actuation state of at least one of the first actuator and the additional actuator in order to control at least one of a tilt of the substrate surface and a height of the substrate surface at the position of inspection in order to maintain the substrate surface substantially at an imaging plane of a detector of the inspection system or a focus of illumination of the inspection system within a selected tolerance level.

2. The system of claim 1, wherein the substrate stage is configured to secure a semiconductor wafer.

3. The system of claim 1, wherein the substrate stage assembly comprises:
    a substrate stage platform; and
    a substrate chuck configured to secure the substrate, wherein the first actuator is operably coupled to the substrate stage platform at a first location and the additional actuator is operably coupled to the substrate stage platform at an additional location.

4. The system of claim 1, wherein the optical assembly of the height detection sub-system is configured to direct the light beam onto the surface of the substrate at substantially the position of inspection of the inspection system; and the one or more optical sensors of the height sensor are configured to detect a relative position of the light beam reflected from the surface of the substrate, wherein the tilt-focus controller is configured to determine a height value of the surface of the substrate based on the measured relative position of the light beam at the sensor.

5. The system of claim 4, wherein the one or more optical sensors of the height sensor comprises:

one or more bicell sensors.

6. The system of claim 4, wherein the one or more optical sensors of the height sensor comprises:

at least one of one or more line CCD sensors and one or more line CMOS sensors.

7. The system of claim 1, wherein the oblique differential interferometer optical assembly comprises:

an optical element configured to separate the light beam from the laser source into a first beam and a second beam and direct the first beam and the second beam onto the substrate at the position of inspection of the inspection system, wherein the first beam and the second beam are orthogonally polarized and transversely separated;

a reflection-transmission flat is configured to reflect back a portion of the first beam and the second beam from the substrate surface back to the optical element, wherein the optical element is configured to recombine the reflected back portion of the first beam and the second beam into a recombined beam;

wherein the first sensor is configured to detect light of at least a first polarization of the recombined beam; and wherein the second sensor is configured to detect light of at least a second polarization of the recombined beam, wherein the tilt-focus controller is further configured to compare the light of the first polarization detected by the first sensor and the light of the second polarization detected by the second sensor in a differential interference detection process in order to determine a tilt of the substrate surface.

8. The system of claim 7, further comprising:

a polarized beam splitter configured to direct light of the first polarization of the combined beam to the first detector and light of the second polarization of the combined beam to a second detector.

9. The system of claim 7, wherein at least one of the first sensor and the second sensor is a photodiode.

10. The system of claim 7, wherein the height detection sub-system comprises:

a height sensor comprising one or more optical sensors configured for substrate height detection, wherein the first beam is directed to the height sensor for substrate height detection by a portion of the oblique differential interferometer optical assembly, wherein the tilt-focus controller is configured to determine a height value of the surface of the substrate based on the measured relative position of the first light beam at the height sensor.

11. The system of claim 7, wherein the optical element is a Wollaston prism.

12. The system of claim 1, wherein the oblique differential interferometer optical assembly comprises:

a first optical element configured to separate the light beam from the laser source into a first beam and a second beam and direct the first beam and the second beam onto the substrate at the position of inspection of the inspection system, wherein the first beam and the second beam are orthogonally polarized and transversely separated;

a second optical element configured to form a recombined beam by combining the first beam and the second beam upon reflection from the substrate surface;

wherein the first sensor configured to detect light of at least a first polarization of the recombined beam; and wherein the second sensor configured to detect light of at least a second polarization of the recombined beam, wherein the tilt-focus controller is further configured to compare the light of the first polarization detected by the first detector and light of the second polarization detected by the second detector in a differential interference detection process in order to determine a tilt of the substrate surface.

13. The system of claim 12, further comprising:

a polarized beam splitter configured to direct light of the first polarization of the combined beam to the first detector and light of the second polarization of the combined beam to a second detector.

14. The system of claim 12, wherein the height detection sub-system comprises:

a height sensor comprising one or more optical sensors configured for substrate height detection, wherein a portion of the combined beam is directed to the height sensor for substrate height detection by a portion of the oblique differential interferometer optical assembly, wherein the tilt-focus controller is configured to determine a height value of the surface of the substrate based on the measured relative position of the first light beam at the height sensor.

15. The system of claim 12, wherein at least one of the first optical element and the second optical element is a Wollaston prism.

16. The system of claim 12, wherein at least one of the first sensor and the second sensor is a photodiode.

17. The system of claim 1, wherein the height detection sub-system and the tilt detection sub-system have a common laser source.

18. The system of claim 1, wherein the height sensor sub-system has a first laser source and the tilt sensor sub-system has a second laser source different from the first laser source.

19. The system of claim 1, wherein at least one of the first actuator and the additional actuator comprise:

a voice coil actuator.

20. The system of claim 1, wherein the additional actuator comprises:

a second actuator.

21. The system of claim 1, wherein the additional actuator comprises:

a second actuator; and at least a third actuator.

22. The system of claim 1, wherein the tilt-focus controller comprises:

a multiple input-multiple output controller.

23. The system of claim 1, wherein the tilt-focus controller is configured to maintain the substrate surface substantially at an imaging plane of a detector or focus of illumination of at least one of a brightfield inspection system and a darkfield inspection system.

24. The system of claim 1, wherein the illumination system of the inspection system comprises:
at least one of a narrowband illumination source and a broadband illumination source.

25. An inspection system with tilt and focus control comprising:
an inspection sub-system including:
an illumination source configured to generate illumination;
a set of illumination optics configured to direct the illumination to an inspection region of a surface of a substrate disposed on a substrate stage of a dynamically adjustable substrate stage assembly;
a detector configured to detect illumination reflected or scattered from the surface of the substrate; and
a set of collection optics configured to collect illumination from the surface of the substrate and direct the illumination to the detector;
a laser source configured to generate a light beam;
a tilt-height detection system including:
a height detection sub-system comprising: an optical assembly; and a height sensor, wherein the height sensor comprises one or more optical sensors configured to measure height of a surface of the substrate at a position of the inspection region of the substrate surface; and
a differential interference contrast tilt detection sub-system configured to measure tilt of the substrate disposed on the substrate stage, wherein the differential interference contrast tilt detection sub-system comprises an oblique differential interferometer optical assembly, wherein the oblique differential interferometer optical assembly comprises a first optical sensor and a second optical sensor;
a first actuator operably coupled to the substrate stage assembly at a first location of the substrate stage assembly and configured to selectively actuate the substrate along a direction substantially perpendicular to the surface of the substrate at the first location of the substrate stage assembly;
an additional actuator operably coupled to the substrate stage assembly at an additional location of the substrate stage assembly and configured to selectively actuate the substrate along a direction substantially perpendicular to the surface of the substrate at the additional location of the substrate stage assembly; and
a tilt-focus controller including one or more processors configured to execute a set of program instructions stored in memory, the tilt-focus controller communicatively coupled to at least the height detection sub-system, the tilt detection sub-system, the first actuator and the additional actuator, wherein the set of program instructions are configured to cause the one or more processors to:
receive one or more height measurements from the height detection sub-system;
receive one or more tilt measurements from the tilt detection sub-system; and
responsive to the measured one or more height measurements and the one or more tilt measurements, selectively adjust an actuation state of at least one of the first actuator and the additional actuator in order to control at least one of a tilt of the substrate surface and a height of the substrate surface at the position of the region of inspection in order to maintain the substrate surface substantially at an imaging plane of a detector of the inspection system or the focus of illumination of the inspection system.

26. The system of claim 25, wherein the inspection sub-system is configured for at least one of brightfield inspection and darkfield inspection.

27. The system of claim 25, wherein the illumination source of the inspection sub-system comprises:
at least one of a narrowband illumination source and a broadband illumination source.

28. The system of claim 25, wherein the detector is configured to detect illumination reflected or scattered from the surface of a semiconductor wafer.

29. The system of claim 25, wherein the substrate stage assembly comprises:
a substrate stage platform; and
a substrate chuck configured to secure the substrate, wherein the first actuator is operably coupled to the substrate stage platform at a first location and the additional actuator is operably coupled to the substrate stage platform at an additional location.

30. The system of claim 25, wherein the optical assembly of the height detection sub-system is configured to direct the light beam onto the surface of the substrate at substantially the position of inspection of the inspection system; and
the one or more optical sensors of the height sensor are configured to detect a relative position of the light beam reflected from the surface of the substrate, wherein the tilt-focus controller is configured to determine a height value of the surface of the substrate based on the measured relative position of the light beam at the sensor.

31. The system of claim 30, wherein the one or more optical sensors of the height sensor comprises:
one or more bicell sensors.

32. The system of claim 30, wherein the one or more optical sensors of the height sensor comprises:
at least one of one or more line CCD sensors and one or more line CMOS sensors.

33. The system of claim 25, wherein the oblique differential interferometer optical assembly comprises:
an optical element configured to separate the light beam from the laser source into a first beam and a second beam and direct the first beam and the second beam onto the substrate at the position of inspection of the inspection system, wherein the first beam and the second beam are orthogonally polarized and transversely separated;
a reflection-transmission flat is configured to reflect back a portion of the first beam and the second beam from the substrate surface back to the optical element, wherein the optical element is configured to recombine the reflected back portion of the first beam and the second beam into a recombined beam;
wherein the first sensor is configured to detect light of at least a first polarization of the recombined beam; and
wherein the second sensor is configured to detect light of at least a second polarization of the recombined beam, wherein the tilt-focus controller is further configured to compare the light of the first polarization detected by the first sensor and the light of the second polarization detected by the second sensor in a differential interference detection process in order to determine a tilt of the substrate surface.

34. The system of claim 33, wherein the height detection sub-system comprises:
a height sensor including one or more optical sensors configured for substrate height detection, wherein a portion of the combined beam is directed to the height sensor for substrate height detection by a portion of the oblique differential interferometer optical assembly, wherein the tilt-focus controller is configured to determine a height value of the surface of the substrate based on the measured relative position of the first light beam at the height sensor.

35. The system of claim 33, wherein the optical element is a Wollaston prism.

36. The system of claim 25, wherein the oblique differential interferometer optical assembly comprises:
a first optical element configured to separate the light beam from the laser source into a first beam and a second beam and direct the first beam and the second beam onto the substrate at the position of inspection of the inspection system, wherein the first beam and the second beam are orthogonally polarized and transversely separated;
a second optical element configured to form a recombined beam by combining the first beam and the second beam upon reflection from the substrate surface;
wherein the first sensor configured to detect light of at least a first polarization of the recombined beam; and
wherein the second sensor configured to detect light of at least a second polarization of the recombined beam, wherein the tilt-focus controller is further configured to compare the light of the first polarization detected by the first detector and light of the second polarization detected by the second detector in a differential interference detection process in order to determine a tilt of the substrate surface.

37. The system of claim 36, wherein the height detection sub-system comprises:
a height sensor including one or more optical sensors configured for substrate height detection, wherein a portion of the combined beam is directed to the height sensor for substrate height detection by a portion of the oblique differential interferometer optical assembly, wherein the tilt-focus controller is configured to determine a height value of the surface of the substrate based on the measured relative position of the first light beam at the height sensor.

38. The system of claim 36, wherein at least one of the first optical element and the second optical element is a Wollaston prism.

39. The system of claim 36, wherein at least one of the first sensor and the second sensor is a photodiode.

40. The system of claim 25, wherein the height detection sub-system and the tilt detection sub-system have a common laser source.

41. The system of claim 25, wherein the height sensor sub-system has a first laser source and the tilt sensor sub-system has a second laser source different from the first laser source.

42. The system of claim 25, wherein at least one of the first actuator and the additional actuator comprise:
a voice coil actuator.

43. The system of claim 25, wherein the additional actuator comprises:
a second actuator.

44. The system of claim 25, wherein the additional actuator comprises:
a second actuator; and
at least a third actuator.

45. The system of claim 25, wherein the tilt-focus controller comprises:
a multiple input-multiple output controller.

* * * * *